(12) United States Patent
Kuehn

(10) Patent No.: US 8,357,195 B2
(45) Date of Patent: Jan. 22, 2013

(54) CATHETER BASED ANNULOPLASTY SYSTEM AND METHOD

(75) Inventor: Stephen Kuehn, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 266 days.

(21) Appl. No.: 12/761,007

(22) Filed: Apr. 15, 2010

(65) Prior Publication Data

US 2011/0257728 A1 Oct. 20, 2011

(51) Int. Cl.
*A61F 2/24* (2006.01)

(52) U.S. Cl. ....................................................... 623/2.37

(58) Field of Classification Search .................. 623/1.11, 623/2.36–2.42
See application file for complete search history.

(56) References Cited

U.S. PATENT DOCUMENTS

| | | | |
|---|---|---|---|
| 6,210,432 B1 | 4/2001 | Solem et al. | |
| 6,332,893 B1 | 12/2001 | Mortier et al. | |
| 6,602,288 B1 | 8/2003 | Cosgrove et al. | |
| 6,702,835 B2 | 3/2004 | Ginn | |
| 6,723,038 B1 | 4/2004 | Schroeder et al. | |
| 6,776,784 B2 | 8/2004 | Ginn | |
| 6,962,605 B2 | 11/2005 | Cosgrove et al. | |
| 6,986,775 B2 | 1/2006 | Morales et al. | |
| 6,989,028 B2 | 1/2006 | Lashinski et al. | |
| 6,997,950 B2 | 2/2006 | Chawla | |
| 6,997,951 B2 | 2/2006 | Solem et al. | |
| 7,011,682 B2 | 3/2006 | Lashinski et al. | |
| 7,037,334 B1 | 5/2006 | Hlavka et al. | |
| 7,044,967 B1 | 5/2006 | Solem et al. | |
| 7,056,325 B1 | 6/2006 | Makower et al. | |
| 7,090,695 B2 | 8/2006 | Solem et al. | |
| 7,166,127 B2 | 1/2007 | Spence et al. | |
| 7,211,110 B2 | 5/2007 | Rowe et al | |
| 7,220,265 B2 | 5/2007 | Chanduszko et al. | |
| 7,296,577 B2 | 11/2007 | Lashinski et al. | |
| 7,311,728 B2 | 12/2007 | Solem et al. | |
| 7,431,692 B2 | 10/2008 | Zollinger et al. | |
| 7,431,726 B2 | 10/2008 | Spence et al. | |
| 7,588,582 B2 | 9/2009 | Starksen et al. | |
| 7,635,386 B1 | 12/2009 | Gammie | |
| 7,637,945 B2 | 12/2009 | Solem et al. | |
| 7,666,193 B2 | 2/2010 | Starksen et al. | |
| 7,699,892 B2 | 4/2010 | Rafiee et al. | |
| 7,717,954 B2 | 5/2010 | Solem et al. | |
| 7,758,637 B2 | 7/2010 | Starksen et al. | |
| 2003/0105519 A1 | 6/2003 | Fasol et al. | |
| 2004/0193191 A1 | 9/2004 | Starksen et al. | |
| 2004/0220596 A1 | 11/2004 | Frazier et al. | |
| 2004/0243227 A1 | 12/2004 | Starksen et al. | |
| 2005/0107810 A1 | 5/2005 | Morales et al. | |
| 2005/0107811 A1 | 5/2005 | Starksen et al. | |
| 2005/0107812 A1 | 5/2005 | Starksen et al. | |
| 2005/0125011 A1 | 6/2005 | Spence et al. | |
| 2005/0177180 A1 | 8/2005 | Kaganov et al. | |

(Continued)

FOREIGN PATENT DOCUMENTS

WO 2008/129405 10/2008
(Continued)

*Primary Examiner* — William H Matthews

(57) ABSTRACT

A catheter-based annuloplasty system for use in repairing a heart valve having leaflets and a valve annulus, includes a delivery catheter having a proximal end and a distal end, and an expandable stent disposed on the distal end of the catheter. An adjustable annuloplasty ring is disposed on the expandable stent and is configured to expand and contract in response to expansion and contraction of the stent.

24 Claims, 5 Drawing Sheets

U.S. PATENT DOCUMENTS

| | | |
|---|---|---|
| 2005/0187568 A1 | 8/2005 | Klenk et al. |
| 2005/0197696 A1 | 9/2005 | Duran |
| 2005/0267495 A1 | 12/2005 | Ginn et al. |
| 2005/0273138 A1 | 12/2005 | To et al. |
| 2006/0025787 A1 | 2/2006 | Morales et al. |
| 2006/0052821 A1 | 3/2006 | Abbott et al. |
| 2006/0095025 A1 | 5/2006 | Levine et al. |
| 2007/0010857 A1 | 1/2007 | Sugimoto et al. |
| 2007/0055206 A1 | 3/2007 | To et al. |
| 2007/0067028 A1 | 3/2007 | Wright et al. |
| 2007/0073315 A1 | 3/2007 | Ginn et al. |
| 2007/0112424 A1 | 5/2007 | Spence et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2008/0228032 A1 | 9/2008 | Starksen et al. |
| 2008/0228165 A1 | 9/2008 | Spence et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0275503 A1 | 11/2008 | Spence et al. |
| 2008/0281411 A1 * | 11/2008 | Berreklouw ................. 623/2.11 |
| 2008/0294177 A1 | 11/2008 | To et al. |
| 2009/0076547 A1 | 3/2009 | Sugimoto et al. |
| 2009/0209950 A1 | 8/2009 | Starksen |
| 2009/0222083 A1 | 9/2009 | Nguyen et al. |
| 2009/0234318 A1 | 9/2009 | Loulmet et al. |
| 2010/0023056 A1 | 1/2010 | Johansson et al. |
| 2010/0030328 A1 | 2/2010 | Seguin et al. |
| 2010/0070028 A1 | 3/2010 | Sugimoto |
| 2010/0076549 A1 * | 3/2010 | Keidar et al. ................. 623/2.36 |
| 2010/0094248 A1 | 4/2010 | Nguyen et al. |
| 2010/0161042 A1 | 6/2010 | Maisano et al. |

FOREIGN PATENT DOCUMENTS

| | | |
|---|---|---|
| WO | WO2010/004546 | 1/2010 |

* cited by examiner

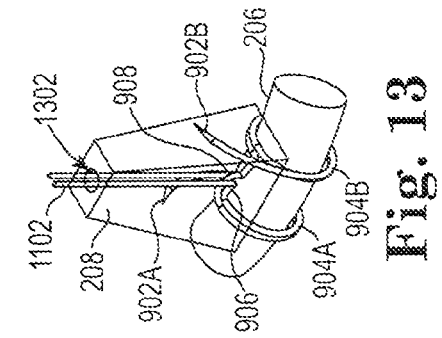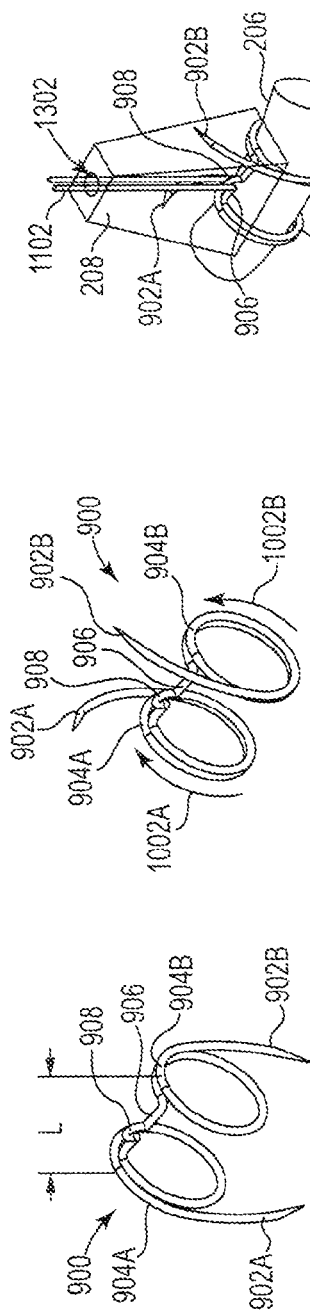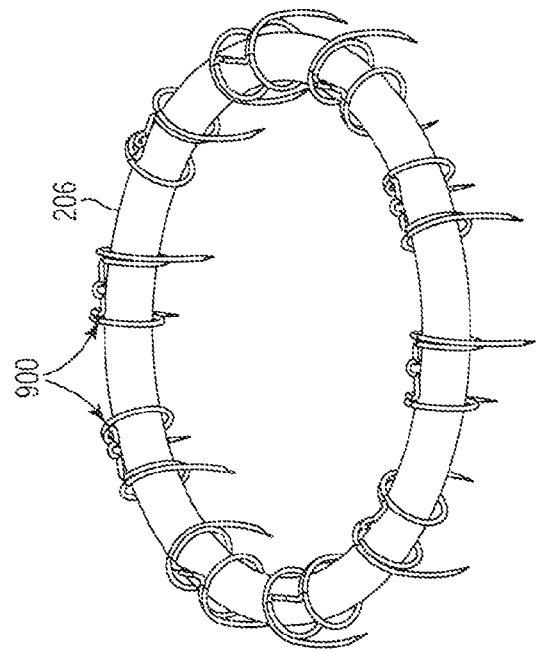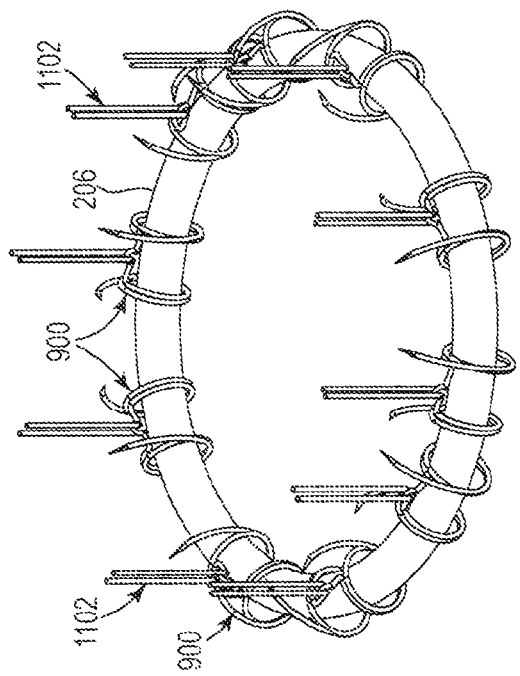

CATHETER BASED ANNULOPLASTY SYSTEM AND METHOD

BACKGROUND

The present invention relates generally to annuloplasty prostheses and methods for repair of heart valves. More particularly, it relates to annuloplasty rings, and related instruments and procedures, for reconstructing and remodeling a valve annulus of a patient's heart, for example a mitral valve annulus.

Heart valves, such as the mitral, tricuspid, aortic, and pulmonary valves, are sometimes damaged by disease or by aging, resulting in problems with the proper functioning of the valve. Heart valve problems generally take one of two forms: stenosis, in which a valve does not open completely or the opening is too small, resulting in restricted blood flow; or insufficiency or regurgitation, in which blood leaks backward across a valve that should be closed.

Annuloplasty prostheses, generally categorized as either annuloplasty rings or annuloplasty bands, are employed in conjunction with valvular reconstructive surgery to assist in the correction of heart valve defects such as stenosis and valvular insufficiency. There are two atrio-ventricular valves in the heart. The mitral valve is located on the left side of the heart, and the tricuspid valve is located on the right side. Anatomically speaking, each valve type forms or defines a valve annulus and valve leaflets.

Both valves can be subjected to or incur damage that requires the valve in question be repaired or replaced. The effects of valvular dysfunction vary. For example, mitral regurgitation, a complication of end-stage cardiomyopathy, has more severe physiological consequences to the patient as compared to lone tricuspid valve regurgitation. Regardless, many of the defects are associated with dilation of the valve annulus. This dilation not only prevents competence of the valve, but also results in distortion of the normal shape of the valve orifice. Remodeling of the annulus is therefore central to most reconstructive procedures on the mitral and tricuspid valves. In this regard, clinical experience has shown that repair of the valve, when technically possible, produces better long-term results as compared to valve replacement.

Many procedures have been described to correct the pathology of the valve leaflets and their associated chordae tendinae and papillary muscles. For example, with respect to the mitral valve, two leaflets are present, the anterior leaflet and the posterior leaflet, such that the mitral valve annulus is commonly described as having an anterior aspect and a posterior aspect. With this in mind, in mitral repairs, it is considered important to preserve the normal distance between the two fibrous trigones. The trigones essentially straddle the anterior aspect of the annulus. A significant surgical diminution of the inter-trigonal distance may cause left ventricular outflow obstruction. Thus, it is desirable to maintain the natural inter-trigonal distance during and following mitral valve repair surgery.

Consequently, when a mitral valve is repaired, the result is generally a reduction of the size of the posterior aspect of the mitral valve annulus. As part of the mitral valve repair, the involved segment of the annulus is diminished (i.e., constricted) so that the leaflets may coapt correctly on closing, or the annulus is stabilized to prevent post-operative dilation from occurring, either as frequently achieved by implantation of a prosthetic ring or band at the level of the valve annulus in the atrium. The purpose of the ring or band is to restrict and/or support the annulus to correct and/or prevent the valvular insufficiency. However, it is important not to overly restrict the annulus as an unacceptable valvular stenosis or Systolic Anterior Motion (SAM) of the anterior leaflet may result. In tricuspid valve repair, constriction of the annulus usually takes place in a posterior leaflet segment and in a small portion of the adjacent anterior leaflet. The septal leaflet segment is not usually required to be shortened.

Previously, valve repair or replacement required openheart surgery with its attendant risks, expense, and extended recovery time. Open-heart surgery also requires cardiopulmonary bypass with risk of thrombosis, stroke, and infarction. More recently, flexible valve prostheses and various delivery devices have been developed so that replacement valves can be implanted transvenously using minimally invasive techniques.

SUMMARY

One embodiment is directed to a catheter-based annuloplasty system for use in repairing a heart valve having leaflets and a valve annulus in a beating heart. The system includes a delivery catheter having a proximal end and a distal end, and an expandable stent disposed on the distal end of the catheter. An adjustable annuloplasty ring is disposed on the expandable stent and is configured to expand and contract in response to expansion and contraction of the stent. In one embodiment, the delivery catheter is configured to deliver the annuloplasty ring to the endocardial surface of the valve annulus.

Another embodiment is directed to an annuloplasty prosthesis for repairing a heart valve having a valve annulus. The annuloplasty prosthesis includes an adjustable ring comprising a plurality of interconnected cylindrically-shaped ring segments, and has a first end co-axially aligned with and inserted into a second end of the adjustable ring. A plurality of tissue attachment members is attached to the adjustable ring. The tissue attachment members are shaped for penetration into the valve annulus and are configured to be triggered from a tension state to a relaxed state.

Yet another embodiment is directed to a method of repairing a heart valve comprising leaflets and a valve annulus. The method includes delivering an adjustable ring having tissue attachment members to a location adjacent to the heart valve via a catheter, and extending a self-expanding stent outside of the catheter, thereby causing an expansion of the adjustable ring. The tissue attachment members are triggered, thereby causing the adjustable ring to be anchored to the valve annulus. The self-expanding stent is contracted, thereby causing a reduction in size of the adjustable ring and the valve annulus. The adjustable ring is locked into position and the delivery catheter is removed.

BRIEF DESCRIPTION OF THE DRAWINGS

FIG. 9 is a diagram illustrating a tissue attachment member in a relaxed state according to one embodiment.

FIG. 10 is a diagram illustrating the tissue attachment member shown in FIG. 9 in a tension state according to one embodiment.

FIG. 11 is a diagram illustrating the adjustable ring shown in FIGS. 3 and 4 including tissue attachment members in a tension state according to one embodiment.

FIG. 12 is a diagram illustrating the adjustable ring shown in FIG. 11 with the tissue attachment members in a relaxed state according to one embodiment.

FIG. 13 is a diagram illustrating a tissue attachment retaining member according to one embodiment.

DETAILED DESCRIPTION

The terms "distal" and "proximal" are used herein with reference to the treating clinician during the use of the catheter system; "Distal" indicates an apparatus portion distant from, or a direction away from the clinician and "proximal" indicates an apparatus portion near to, or a direction towards the clinician. Additionally, the term "annuloplasty" is used herein to mean modification/reconstruction of a defective heart valve.

Embodiments disclosed herein include devices and methods for treating regurgitation in cardiac valves. While these devices and methods are described below in terms of being used to treat mitral regurgitation, it will be apparent to those skilled in the art that the devices could also be used on other cardiac valves. Embodiments disclosed herein include minimally-invasive, off-pump, catheter-based systems and methods for attaching a prosthetic ring to the annulus of the mitral valve of a beating heart, and adjusting the ring, thereby reshaping the mitral valve annulus so that the anterior and posterior leaflets of the mitral valve co-apt during ventricular contraction.

Figure 1:
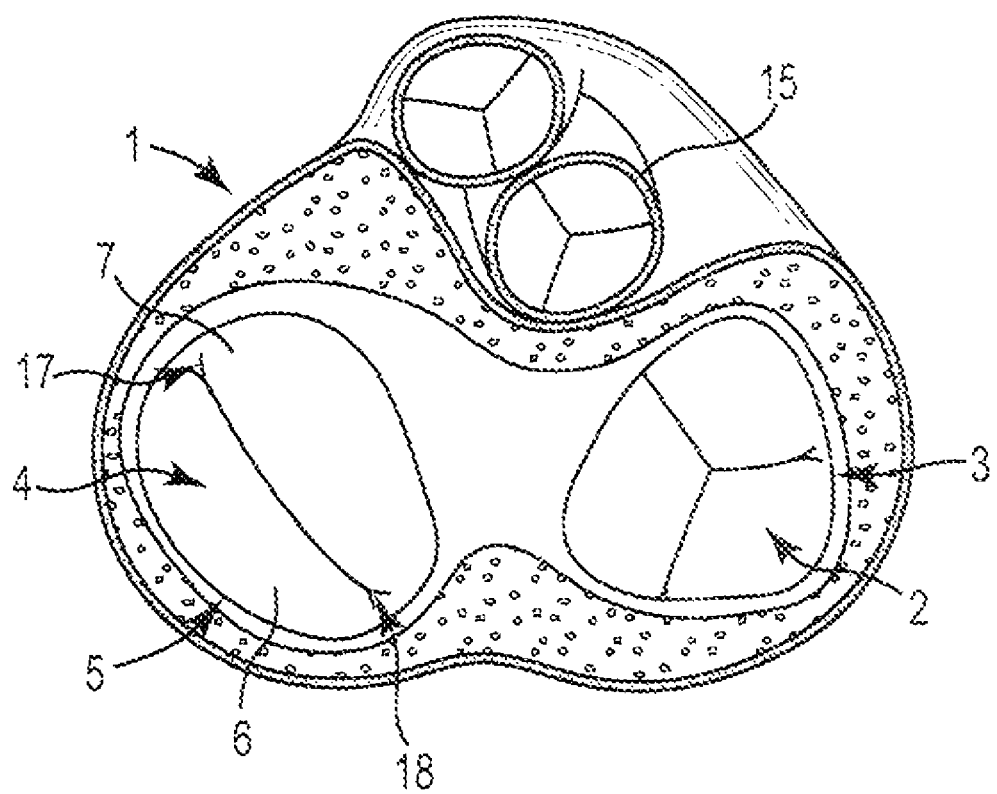
FIG. 1 is a cross-sectional schematic view of a heart showing the location of the heart valves.

FIG. 1 shows a schematic cross-sectional view of a heart 1 having tricuspid valve 2, tricuspid valve annulus 3, mitral valve 4, and mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets. FIG. 1 also shows the aorta 15, which is located adjacent to the wall of the left atrium on the anterior side of the mitral valve. Also shown in the figure are the posterior commisure 17 and the anterior commisure 18.

Figure 2:
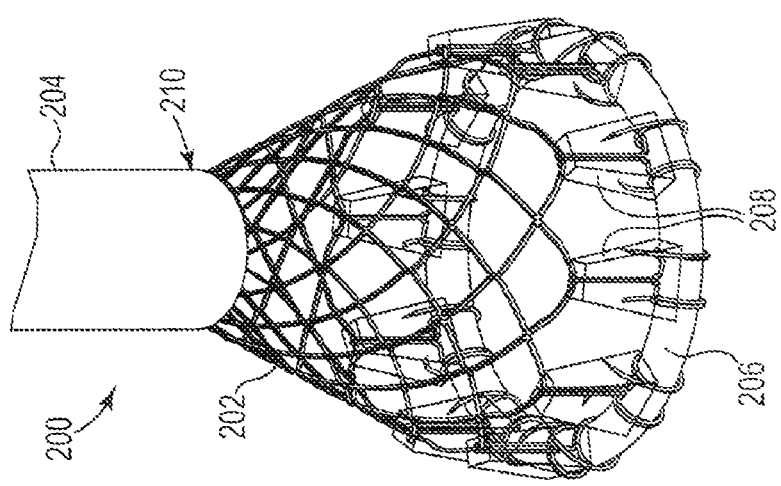
FIG. 2 is a diagram illustrating an annuloplasty system for use in repairing a heart valve according to one embodiment.

FIG. 2 is a diagram illustrating a catheter-based annuloplasty system 200 for use in repairing a heart valve having leaflets and a valve annulus according to one embodiment. In one embodiment, annuloplasty system 200 is configured to be used off-pump to repair the heart valve of a beating heart. Annuloplasty system 200 includes expandable stent 202, delivery catheter 204, adjustable annuloplasty ring 206, and a plurality of tissue attachment retaining members 208. The annuloplasty ring 206 according to one embodiment is particularly adapted to repair one of the atrio-ventricular valves, such as the mitral valve 4 or the tricuspid valve 2. The annuloplasty ring 206 illustrated in FIG. 2 is configured for repair of the annulus 5 of the mitral valve 4. It will be understood that other shapes may be incorporated for other valve annulus anatomies (e.g., the tricuspid valve annulus 3). Thus, the present invention is not limited to mitral valve annuloplasty.

Stent 202 and catheter 204 comprise a catheter-based delivery system 210 for delivering ring 206 adjacent to a valve annulus for attachment thereto. The catheter 204 includes a proximal end and a distal end. The stent 202 is disposed on the distal end of the catheter 204. The stent 202 and the ring 206 are initially collapsed and thereby reduced in diameter, mounted in the catheter 204, and advanced through the circulatory system of a patient. The ring 206 is disposed on a distal end of the stent 202, and is releasably carried within the delivery catheter 204 to a position near the valve annulus. Stent 202 is then gradually extended beyond the distal tip of the catheter 204. In the illustrated embodiment, stent 202 is a self-expanding stent, and automatically increases in size as it is extended outside of the catheter 204. Stent 202 and tissue attachment retaining members 208 according to one embodiment are formed of a shape memory material. In one embodiment, stent 202 comprises a NITINOL™ framework.

In one embodiment, the ring 206 has an adjustable size (e.g., circumference and diameter), and is configured to be adjusted via stent 202 during and after installation around the valve annulus. The ring 206 is configured to expand and contract in response to expansion and contraction, respectively, of the stent 202. As stent 202 is extended outside of the catheter 204, the expansion of the distal end of the stent 202 causes a corresponding expansion in the ring 206. As stent 202 is returned inside of the catheter 204, the contraction of the distal end of the stent 202 causes a corresponding contraction in the ring 206. Stent 202 is used to adjust the size of ring 206 until the ring 206 reaches an appropriate size for attachment to the valve annulus. When the ring 206 reaches the appropriate size, tissue attachment members 900 (FIGS. 9-12) are triggered to attach the ring 206 to the valve annulus. In one embodiment, the annuloplasty procedure described herein is performed using three-dimensional echocardiographic guidance.

Figure 3:
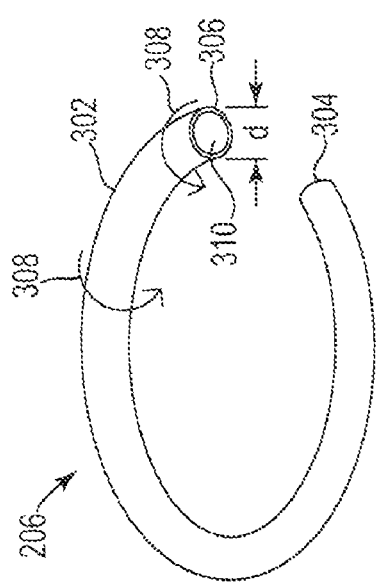
FIG. 3 is a diagram illustrating one embodiment of the adjustable ring of the annuloplasty system shown in FIG. 2.
Figure 4:
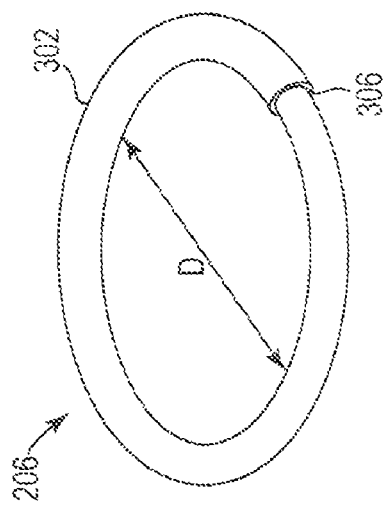
FIG. 4 is a diagram illustrating the adjustable ring shown in FIG. 3 in a closed configuration according to one embodiment.

FIG. 3 is a diagram illustrating one embodiment of the adjustable ring 206 of the annuloplasty system 200 shown in FIG. 2. The ring 206 is formed from a tube 302 having a channel 310 therethrough. The ring 206 is formed of any medically acceptable implantable biocompatible material. A first end 304 of the ring co-axially aligns with and inserts into a second end 306 of the ring 206 to form the ring shape. In one embodiment, the internal diameter or tube diameter, d, of selected portions of the ring 206 may be increased in size by axially twisting those portions, as indicated by arrows 308. The second end 306 is increased in size in this manner, to allow the first end 304 to fit inside the second end 306 in a co-axial manner. FIG. 4 is a diagram illustrating the adjustable ring 206 in a closed configuration according to one embodiment, after the first end 304 has been inserted inside of the second end 306. The overall diameter, D, and circumference of the ring 206 can be decreased by pushing the first end 304 farther into the second end 306, and can be increased by pulling the first end 304 in an outward direction from the second end 306. In one embodiment, contracting or collapsing the stent 202 (FIG. 2) causes the first end 304 to extend farther into the second end 306, thereby reducing the overall diameter, D, and expanding the stent 202 causes the first end 304 to be pulled back toward the second end 306, thereby increasing the overall diameter, D.

Figure 5A:
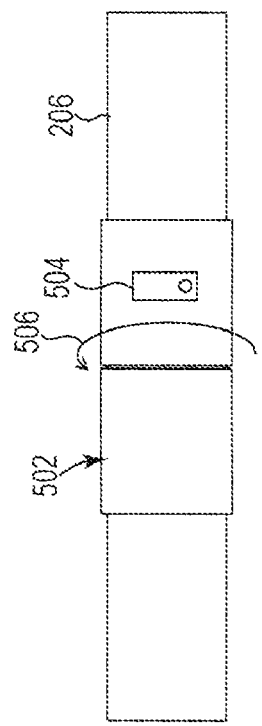
FIGS. 5A-5C are diagrams illustrating a locking mechanism of the adjustable ring shown in FIGS. 3 and 4 according to one embodiment.
Figures 5B, 5C:
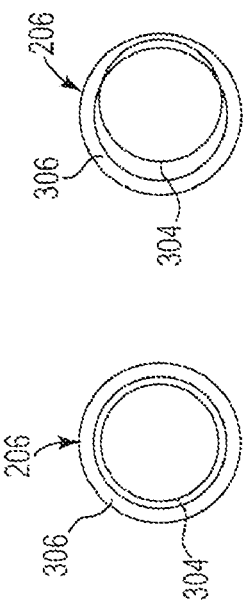

FIG. 5A is a diagram illustrating a locking mechanism 502 of the adjustable ring 206 shown in FIGS. 3 and 4 according to one embodiment. In the illustrated embodiment, locking mechanism 502 is a locking sleeve that is positioned at the second end 306 of the ring 206. Locking mechanism 502 includes an attachment member 504 for attaching a suture or wire (not shown) thereto. Pulling on the suture attached to the attachment member 504 causes the locking sleeve 502 to rotate as indicated by arrow 506, which locks the ring 206 at the current size and prevents further size adjustments to the ring. The locking mechanism is configured to lock a surface of the adjustable ring between asymmetrical lumens within the locking mechanism. FIG. 5B is a diagram illustrating the adjustable ring 206 in an unlocked state according to one embodiment. As shown in FIG. 5B, the first end 304 of the ring 206 is positioned inside of the second end 306 of the ring 206, and the ends 304 and 306 are axially aligned within the lumen. FIG. 5C is a diagram illustrating the adjustable ring 206 in a locked state according to one embodiment. As shown in FIG. 5C, the ends 304 and 306 are no longer axially aligned within the lumen. The locking mechanism 502 according to one embodiment causes the first end 304 to interfere with the second end 306 as shown in FIG. 5C, which results in the ring 206 being held in place at its current size.

Figure 6:
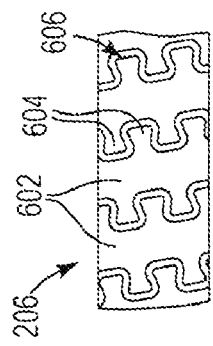
FIG. 6 is a diagram illustrating a close-up view of a portion of the adjustable ring shown in FIGS. 3 and 4 in an expanded state according to one embodiment.

FIG. 6 is a diagram illustrating a close-up view of a portion of the adjustable ring 206 shown in FIGS. 3 and 4 in an expanded state according to one embodiment. In the illustrated embodiment, adjustable ring 206 is formed from a plurality of interconnected cylindrically-shaped ring segments 602. Each segment 602 includes a plurality of tabs 604 that extend away from the body of the segment parallel to the surface of the ring 206. Adjacent tabs 604 in each segment 602 are separated by a gap 606. Each tab 604 of each segment 602 is positioned within one of the gaps 606 of an adjacent segment 602. The tab design restricts movement axially to the width of the gap while allowing the ring to bend in any direction. By performing an axial twisting on the ring 206 in the direction shown by arrows 308 in FIG. 3 causes a separation between adjacent segments 602 (as shown in FIG. 6), which causes the internal diameter, d (FIG. 3), of the ring 206 to increase.

Figure 7:
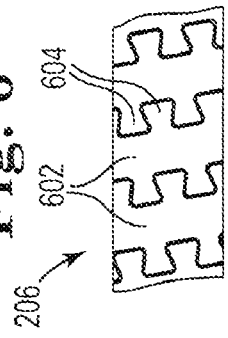
FIG. 7 is a diagram illustrating a close-up view of a portion of the adjustable ring shown in FIGS. 3 and 4 in a compressed state according to one embodiment.

FIG. 7 is a diagram illustrating a close-up view of a portion of the adjustable ring 206 shown in FIGS. 3 and 4 in a compressed state according to one embodiment. When ring 206 is in an expanded state as shown in FIG. 6, providing a rotational force to the ring 206 in the opposite direction to that shown by arrows 308 in FIG. 3 causes the separation between adjacent segments 602 to be reduced or eliminated (as shown in FIG. 7), which causes the internal diameter, d (FIG. 3), of the ring 206 to decrease.

Figure 8:
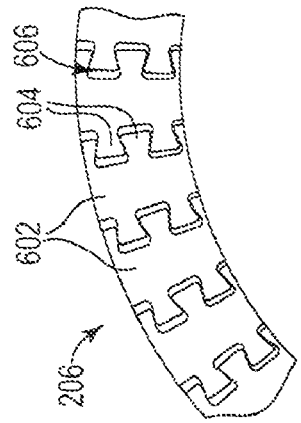
FIG. 8 is a diagram illustrating a close-up view of a portion of the adjustable ring shown in FIGS. 3 and 4 while the ring is in a circular configuration according to one embodiment.

FIG. 8 is a diagram illustrating a close-up view of a portion of the adjustable ring 206 shown in FIGS. 3 and 4 while the ring 206 is in a circular configuration according to one embodiment. As shown in FIG. 8, when ring 206 is curved into a circular configuration, such as that shown in FIG. 4, there is a larger separation between adjacent segments 602 near the outer radius of the ring 206 (i.e., near the top of FIG. 8), and a smaller separation between adjacent segments 602 near the inner radius of the ring 206 (i.e., near the bottom of FIG. 8).

FIG. 9 is a diagram illustrating a tissue attachment member 900 in a relaxed state according to one embodiment. Tissue attachment member 900 is shaped for penetration into the valve annulus and is configured to be triggered from a tension state (maintained during delivery) to a relaxed state (to attach the ring 206 to the valve annulus). Tissue attachment member 900 includes first and second prong portions 902A and 902B, first and second circular spring portions 904A and 904B, and a cross member 906, which are all formed from NITINOL™ wire in one embodiment. The cross member 906 connects the first and second circular spring portions 904A and 904B, and includes a feature such as a bump 908 that is configured to be connected to a suture to hold the ring 206 adjacent to the stent 202. The prong portions 902A and 902B extend from the circular spring portions 904A and 904B, respectively. The first and second circular spring portions 904A and 904B and separated by a distance L, which is about two millimeters in one embodiment. In the illustrated embodiment, tissue attachment member 900 is in a relaxed state.

FIG. 10 is a diagram illustrating the tissue attachment member 900 shown in FIG. 9 in a spring-loaded or tension state according to one embodiment. Tissue attachment member 900 is changed from the relaxed state (as shown in FIG. 9) to the tension state (as shown in FIG. 10) by applying a force to move the prong portions 902A and 902B in the direction indicated by arrows 1002A and 1002B, respectively, which causes the tissue attachment member 900 to be spring-loaded. If the force is removed from the prong portions 902A and 902B, the prong portions 902A and 902B spring back to the relaxed state shown in FIG. 9.

FIG. 11 is a diagram illustrating the adjustable ring 206 shown in FIGS. 3 and 4 including tissue attachment members 900 in a spring-loaded or tension state according to one embodiment. As shown in FIG. 11, ring 206 extends through the circular spring portions 904A and 904B of each tissue attachment member 900. Thus, each tissue attachment member 900 is attached to the ring 206 via the circular spring portions 904A and 904B. A suture 1102 is attached to the bump 908 of each tissue attachment member 900. The sutures 1102 are used to hold the ring 206 adjacent to the distal end of the stent 202 (FIG. 2). In one embodiment, a tissue attachment retaining member 208 (FIG. 2) is configured to be positioned over the prong portions 902A and 902B of each tissue attachment member 900 to hold the tissue attachment member 900 in the tension state.

The tissue attachment members 900 are used to attach the ring 206 to the valve annulus. When ring 206 is in position adjacent to the annulus, stent 202 is pulled away from ring 206, which causes tissue attachment retaining members 208 to be lifted away from prong portions 902A and 902B of the tissue attachment members 900. When tissue attachment retaining members 208 are removed from prong portions 902A and 902B, the prong portions 902A and 902B spring toward the relaxed state (FIG. 12) and penetrate the annulus tissue.

FIG. 12 is a diagram illustrating the adjustable ring 206 shown in FIG. 11 with the tissue attachment members 900 in the relaxed state according to one embodiment. As shown in FIG. 12, the sutures 1102 have been cut or released, and the tissue attachment retaining members 208 have been lifted away from the prong portions 902A and 902B, thereby causing the prong portions 902A and 902B to spring toward the relaxed state, penetrate the annulus tissue, and anchor the ring 206 to the annulus.

FIG. 13 is a diagram illustrating a tissue attachment retaining member 208 according to one embodiment. Retaining member 208 is configured to release the tissue attachment members 900 from the tension state when the ring 206 is adjacent to the valve annulus, thereby causing the tissue attachment members 900 to transition to the relaxed state and anchor the ring 206 to the valve annulus. As shown in FIG. 13, retaining member 208 slides over prong portions 902A and 902B of tissue attachment member 900, and thereby holds the tissue attachment member 900 in the tension state. Suture 1102 extends through a hole 1302 at the top of the retaining member 208. Pulling retaining member 208 upward and away from the prong portions 902A and 902B triggers the tissue attachment member 900 to transition from the tension state to the relaxed state. In one embodiment, the ring 206 is configured to be adjusted in size after the ring 206 has been anchored to the valve annulus.

Figure 14:
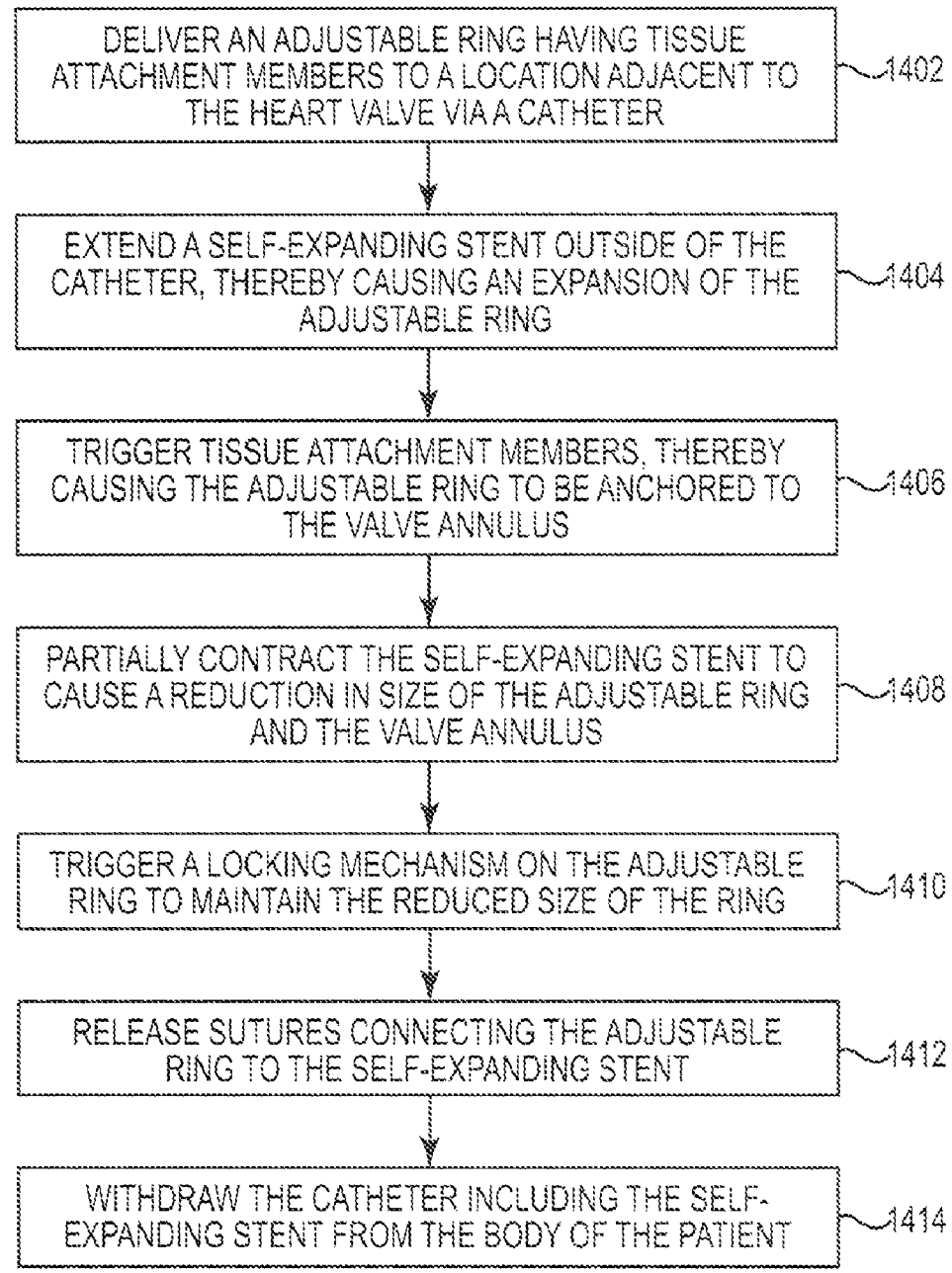
FIG. 14 is a flow diagram illustrating a method of repairing a heart valve according to one embodiment.

FIG. 14 is a flow diagram illustrating a method 1400 of repairing a heart valve comprising leaflets and a valve annulus according to one embodiment. In one embodiment, method 1400 is performed off-pump to repair the heart valve of a beating heart. At 1402, an adjustable ring 206 having tissue attachment members 900 is delivered to a location adjacent to the heart valve via a catheter 204. In one embodiment, a distal tip of the catheter 204 containing the adjustable ring 206 and a self-expanding stent 202 is advanced through the vascular system of a patient, passes into the left atrium, and is positioned adjacent to the mitral valve annulus. At 1404, the self-expanding stent 202 is extended outside of the catheter 204, thereby causing an expansion of the adjustable ring 206, and causing the adjustable ring 206 to be positioned against the mitral valve annulus. At 1406, tissue attachment members 900 attached to the adjustable ring 206 are triggered, thereby causing the adjustable ring 206 to be anchored to the mitral valve annulus. At 1408, the self-expanding stent 202 is partially contracted, which causes a reduction in size of the adjustable ring 206 and the valve annulus. In one embodiment, the stent 202 is contracted by pushing the catheter forward, causing a portion of the stent 202 to return inside of the catheter 204. Because the ring 206 is securely fastened to the annulus of the mitral valve via the tissue attachment members 900, the diameter and circumference of the annulus is reduced as the size of the ring 206 is reduced at 1408. In one embodiment, the size of the annulus is reduced at 1408 sufficiently so that anterior and posterior leaflets close during ventricular contraction, and regurgitation of blood is reduced. At 1410, a locking mechanism 502 on the ring 206 is triggered after causing the reduction in size of the ring 206 to maintain the reduced size of the ring 206. At 1412, sutures 1102 connecting the ring 206 to the stent 202 are released. At 1414, the delivery catheter 204 including the stent 202 is withdrawn from the body of the patient.

The minimally-invasive, off-pump, catheter-based annuloplasty system and method described herein provides the ability to intervene with patients in both early disease states or in advanced heart failure, and provides advantages over traditional surgical repair devices because traditional open heart surgery is no longer needed.

Although the present disclosure has been described with reference to preferred embodiments, workers skilled in the art will recognize that changes can be made in form and detail without departing from the spirit and scope of the present disclosure.

What is claimed is:

1. A catheter-based annuloplasty system for use in repairing a heart valve having leaflets and a valve annulus, comprising:
   a delivery catheter having a proximal end and a distal end;
   an expandable stent disposed on the distal end of the catheter; and
   an adjustable annuloplasty ring disposed on the expandable stent configured to expand and contract in response to expansion and contraction of the stent, wherein the adjustable ring includes a plurality of tissue attachment members shaped for penetration into the valve annulus and configured to be triggered from a tensioned state to a relaxed state, and wherein the adjustable ring extends through at least one spring portion of each of the tissue attachment members.

2. The annuloplasty system of claim 1, wherein each tissue attachment member comprises:
   a first prong portion extending from a first circular spring portion;
   a second prong portion extending from a second circular spring portion; and
   a cross-member connecting the first and second circular spring portions.

3. The annuloplasty system of claim 2, wherein the adjustable ring extends through the first and second circular spring portions of each of the tissue attachment members.

4. The annuloplasty system of claim 2, wherein the cross-member includes a feature configured to be connected to hold the adjustable ring adjacent to the expandable stent.

5. The annuloplasty system of claim 1, and further comprising:
   a plurality of tissue attachment retaining members disposed on the expandable stent and configured to hold the tissue attachment members in the tensioned state.

6. The annuloplasty system of claim 5, wherein the tissue attachment retaining members are configured to release the tissue attachment members from the tensioned state when the adjustable ring is adjacent to the valve annulus, thereby causing the tissue attachment members to transition to the relaxed state and anchor the adjustable ring to the valve annulus.

7. The annuloplasty system of claim 6, wherein the adjustable ring is configured to be adjusted in size after the adjustable ring has been anchored to the valve annulus.

8. The annuloplasty system of claim 5, wherein the tissue attachment retaining members are formed of a shape memory material.

9. The annuloplasty system of claim 1, wherein the adjustable ring comprises a plurality of interconnected cylindrically-shaped ring segments.

10. The annuloplasty system of claim 9, wherein each of the ring segments includes a plurality of tabs that extend away from a body of the segment parallel to a surface of the adjustable ring.

11. The annuloplasty system of claim 10, wherein adjacent ones of the tabs in each ring segment are separated by a gap, and wherein each tab of each segment is positioned within one of the gaps of an adjacent segment.

12. The annuloplasty system of claim 9, wherein axial twisting of the adjustable ring causes a separation between adjacent segments and an increase in an internal diameter of the adjustable ring.

13. The annuloplasty system of claim 9, wherein a first end of the ring is co-axially aligned with and inserted into a second end of the ring.

14. The annuloplasty system of claim 13, wherein contraction of the stent causes the first end of the ring to extend farther into the second end of the ring, thereby reducing an overall diameter of the adjustable ring.

15. The annuloplasty system of claim 14, and further comprising a locking mechanism configured to lock the adjustable ring and thereby prevent further size adjustments to the ring.

16. The annuloplasty system of claim 15, wherein the locking mechanism is configured to lock a surface of the adjustable ring between asymmetrical lumens within the locking mechanism.

17. The annuloplasty system of claim 1, wherein the stent is a self-expanding stent formed of a shape memory material.

18. The annuloplasty system of claim 1, wherein the stent is a self-expanding NITINOL™ framework.

19. The annuloplasty system of claim 1, wherein the system is configured to be used off-pump to repair the heart valve of a beating heart.

20. A method of repairing a heart valve comprising leaflets and a valve annulus, the method comprising:
- delivering an adjustable ring having tissue attachment members to a location adjacent to the heart valve via a catheter;
- extending a self-expanding stent outside of the catheter, thereby causing an expansion of the adjustable ring;
- triggering the tissue attachment members, thereby causing the adjustable ring to be anchored to the valve annulus; and
- contracting the self-expanding stent, thereby causing a reduction in size of the adjustable ring and the valve annulus.

21. The method of claim 20, and further comprising:
- triggering a locking mechanism on the adjustable ring after causing the reduction in size of the adjustable ring to maintain the reduced size of the ring.

22. The method of claim 20, wherein the method is performed off-pump to repair the heart valve of a beating heart.

23. A catheter-based annuloplasty system for use in repairing a heart valve having leaflets and a valve annulus, comprising:
- a delivery catheter having a proximal end and a distal end;
- an expandable stent disposed on the distal end of the catheter;
- an adjustable annuloplasty ring disposed on the expandable stent configured to expand and contract in response to expansion and contraction of the stent, wherein the adjustable ring includes a plurality of tissue attachment members shaped for penetration into the valve annulus and configured to be triggered from a tensioned state to a relaxed state; and
- a plurality of tissue attachment retaining members disposed on the expandable stent and configured to hold the tissue attachment members in the tensioned state.

24. A catheter-based annuloplasty system for use in repairing a heart valve having leaflets and a valve annulus, comprising:
- a delivery catheter having a proximal end and a distal end;
- an expandable stent disposed on the distal end of the catheter; and
- an adjustable annuloplasty ring disposed on the expandable stent configured to expand and contract in response to expansion and contraction of the stent, wherein the adjustable ring comprises a plurality of interconnected cylindrically-shaped ring segments, and wherein each of the ring segments includes a plurality of tabs that extend away from a body of the segment parallel to a surface of the adjustable ring.

\* \* \* \* \*